(12) United States Patent
Puchhammer

(10) Patent No.: US 8,343,234 B2
(45) Date of Patent: *Jan. 1, 2013

(54) HAND PROSTHESIS COMPRISING TWO DRIVE DEVICES

(75) Inventor: Gregor Puchhammer, Vienna (AT)

(73) Assignee: Otto Bock Healthcare GmbH, Duderstadt (DE)

( * ) Notice: Subject to any disclaimer, the term of this patent is extended or adjusted under 35 U.S.C. 154(b) by 259 days.

This patent is subject to a terminal disclaimer.

(21) Appl. No.: 12/097,798

(22) PCT Filed: Dec. 7, 2006

(86) PCT No.: PCT/DE2006/002176
§ 371 (c)(1),
(2), (4) Date: Jun. 17, 2008

(87) PCT Pub. No.: WO2007/076764
PCT Pub. Date: Jul. 12, 2007

(65) Prior Publication Data
US 2008/0262634 A1    Oct. 23, 2008

(30) Foreign Application Priority Data
Dec. 20, 2005   (DE) .......................... 10 2005 061 312

(51) Int. Cl.
*A61F 2/54* (2006.01)
(52) U.S. Cl. .......................................... 623/64; 623/24
(58) Field of Classification Search ............ 623/57, 623/63–65, 24; 901/30, 32, 36, 38
See application file for complete search history.

(56) References Cited

U.S. PATENT DOCUMENTS

| | | | |
|---|---|---|---|
| 1,225,415 A | 5/1917 | Cronemiller | |
| 1,630,277 A | 5/1927 | Smith | |
| 2,433,301 A | 12/1947 | Simpson | |
| 2,553,827 A | 5/1951 | Mason | |
| 2,859,450 A | 11/1958 | Becker | |
| 3,026,534 A | 3/1962 | Brown | |
| 3,694,021 A * | 9/1972 | Mullen | 294/106 |
| 4,114,464 A * | 9/1978 | Schubert et al. | 74/89.14 |
| 4,149,278 A * | 4/1979 | Frosch et al. | 623/62 |
| 4,246,661 A | 1/1981 | Pinson | |

(Continued)

FOREIGN PATENT DOCUMENTS
DE            19854762         6/2000
(Continued)

OTHER PUBLICATIONS

International Search Report for PCT/DE2006/002176, mailed Aug. 3, 2007, 5 pgs.

(Continued)

*Primary Examiner* — William H. Matthews
*Assistant Examiner* — Marcia Hoffman
(74) *Attorney, Agent, or Firm* — Holland and Hart LLP

(57) ABSTRACT

A hand prosthesis includes a chassis and a finger prosthesis articulated to the chassis. A first drive is located in the chassis and is coupled via a force transmission unit to the finger prosthesis for moving the finger prosthesis about a first swiveling axis relative to the chassis. A second drive is located within the finger prosthesis and moves the finger prosthesis about a second swiveling axis relative to the chassis and relative to the first swiveling axis.

19 Claims, 4 Drawing Sheets

U.S. PATENT DOCUMENTS

| | | | |
|---|---|---|---|
| 4,364,593 A * | 12/1982 | Maeda | 294/106 |
| 4,623,354 A | 11/1986 | Childress et al. | |
| 4,685,924 A | 8/1987 | Massey | |
| 4,685,929 A * | 8/1987 | Monestier | 623/64 |
| 4,792,338 A | 12/1988 | Rennerfelt | |
| 4,921,293 A | 5/1990 | Ruoff et al. | |
| 4,955,918 A * | 9/1990 | Lee | 623/24 |
| 5,080,682 A | 1/1992 | Schectman | |
| 5,888,246 A | 3/1999 | Gow | |
| 6,660,043 B2 | 12/2003 | Kajitani et al. | |
| 6,896,704 B1 * | 5/2005 | Higuchi et al. | 623/64 |
| 2003/0195638 A1 | 10/2003 | Kajitani et al. | |
| 2004/0015240 A1 | 1/2004 | Archer et al. | |
| 2004/0103740 A1 * | 6/2004 | Townsend et al. | 74/490.01 |
| 2005/0021154 A1 | 1/2005 | Brimalm | |

FOREIGN PATENT DOCUMENTS

| | | |
|---|---|---|
| DE | 19906294 | 9/2000 |
| DE | 20301116 | 3/2003 |
| DE | 10237373 | 3/2004 |
| EP | 0045818 | 2/1982 |
| EP | 0219478 | 10/1986 |
| EP | 1195151 | 4/2002 |
| FR | 2236478 | 2/1975 |
| GB | 1201182 | 8/1967 |
| GB | 1175830 | 12/1969 |
| GB | 1585256 | 6/1976 |
| GB | 1571140 | 11/1977 |
| JP | 51-125094 U | 10/1976 |
| JP | 2004-351567 A | 12/2004 |
| WO | 03 017876 | 3/2003 |
| WO | WO 03/017880 | 3/2003 |

OTHER PUBLICATIONS

International Search Report and Written Opinion issued in PCT/DE2006/002177, 9 pages, mailed Aug. 3, 2007.

International Search Report and Written Opinion issued in PCT/DE2006/002175, 8 pages, mailed Aug. 3, 2007.

Non-Final Office Action mailed Aug. 21, 2009 for U.S. Appl. No. 12/097,800, 14 pages.

Non-Final Office Action mailed Aug. 28, 2009 for U.S. Appl. No. 12/097,804, 19 pages.

* cited by examiner

HAND PROSTHESIS COMPRISING TWO DRIVE DEVICES

CROSS-REFERENCE TO RELATED APPLICATION

This application is a national stage application, filed pursuant to 35 U.S.C. §371, of PCT/DE2006/002176 filed Dec. 7, 2006, which claims priority to DE 10 2005 061 312.8 filed Dec. 20, 2005, both of which are herein incorporated by reference in their entirety.

TECHNICAL FIELD

The invention relates to a hand prosthesis comprising a chassis, to which at least one finger prosthesis is articulated, said finger prosthesis being movable about at least one swiveling axis by means of a drive.

BACKGROUND

If a hand has to be amputated or has been irreversibly severed from an arm by an accident, the appearance and some of the function of the hand can be replaced by a hand prosthesis. For this purpose, the hand prosthesis must be capable of displacing gripping devices, which may be formed as replicas of fingers, in relation to one another, in order to allow gripping of an object.

Apart from a two-finger gripper, as is known from US 2003/00195638 A1, conventional hand prostheses have a drive that is rigidly connected to a hand chassis by means of a bevel gear mechanism. Depending on the direction of rotation of the drive, the finger prostheses are thereby moved toward or away from one another. This drive may be activated by means of myoelectrical signals. Such a hand prosthesis is described in US 2005/0021154 A1. The appearance of such a hand prosthesis looks less natural.

SUMMARY

An object of the present invention is to provide a hand prosthesis which has a design made to resemble the natural appearance of a hand and has improved functionality.

The hand prosthesis according to the invention comprises a chassis to which at least one finger prosthesis is articulated. The finger prosthesis is movable about at least one swiveling axis by means of a first drive which is connected to the finger prosthesis by means of a force transmission unit. This first drive is located in the chassis, is coupled to the finger prosthesis via the force transmission unit and allows the finger prosthesis to be swiveled about a first swiveling axis. Furthermore, a second drive is located in the finger prosthesis and allows at least one part of the finger prosthesis to be swiveled about a second swiveling axis relative to the first swiveling axis. As a result, it is possible to replicate a complex movement of the fingers very well, without the hand prosthesis as such becoming very large or requiring a complicated mechanism by which the different movements are initiated from a central drive. Preferably, the drives are decoupled from each other, to allow the respective components or parts of the prosthesis to be activated and displaced independently of one another.

In one embodiment, the force transmission unit between the first drive and the finger prosthesis is formed so as to be yielding under pressure, or elastic under bending, and rigid under tension. Conventional hand prostheses provide a rigid coupling between the drive and the finger prosthesis. However, the pressure-yielding or flexurally elastic coupling of the drive to the finger prosthesis according to embodiments of the present invention allows the finger prosthesis to give way under pressure loading of the force transmission unit, which is the effect of a force that brings about closing of the hand or reduction of the angle between the finger prosthesis and the hand chassis.

Apart from creating a natural looking appearance, this also has the effect of minimizing the stress on the mechanical components. The stress on the components is minimized because the sometimes considerable forces, that occur if the finger prostheses happen to knock against an object are not transmitted directly via the force transmission unit to the drive. Rather, the flexurally elastic, preferably resilient, configuration of the force transmission unit allows displacement and conversion of the forces acting on the finger prosthesis into a movement. This movement may take place up to the maximum bending angle of the finger prosthesis.

Another embodiment of the present invention allows an unhindered and reliable, as well as precise, closing movement of the finger prosthesis, starting from an open basic position. The force transmission unit is formed so as to be rigid under tension, such that that tensile forces are transmitted as far as possible without the force transmission unit undergoing any elongation. For this purpose, the force transmission unit may comprise a cable, stranded wire or fiber via which the tensile forces are transmitted. This cable, stranded-wire or fiber component may be produced from a wire cable or high-strength fibers such as carbon fibers, aramid or glass fibers, natural fibers or other synthetic fibers. The cable, stranded-wire or fiber component may be formed as a closed, open or twisted loop.

In one embodiment, the force transmission unit has an elastomer component, by which it is possible to set the flexure or elasticity of the force transmission unit over a wide range. A suitable-elastomer material may at least partially enclose or completely take up the cable or fiber component. This produces a body that is dimensionally stable in the position of rest, which has very high tensile forces from the incorporated cable or fiber component and has desired elastic characteristics under bending and pressure.

Alternatively, the force transmission unit may be configured as a spring-damper unit, in particular as a pneumatic unit. The volume of air is compressed under pressure loading, expands once the force of the pressure is no longer applied and brings about a return displacement of a pneumatic piston, and consequently of the finger prosthesis.

For coupling the force transmission unit to the drive and the finger prosthesis, bearing bushings are embedded in the force transmission unit. These bearing bushings may be enclosed by the elastomer element or the elastomer component, and are located within the cable or fiber component, for example, within the cable or fiber loop.

To provide a return movement of a finger prosthesis bent in the direction of the inner surface of the hand chassis, the force transmission unit is formed in a resiliently elastic manner. When not being subjected to a tensile force, the finger prosthesis is moved back into a starting position by the drive or by a transmission element coupled to the drive. This starting position corresponds to a slightly opened hand. The force transmission unit is consequently capable of transmitting a limited compressive force. A corresponding articulation or formation of the force transmission unit allows slight over-extension of the finger prostheses, starting from the basic position. The spring rate of the force transmission unit is, in this case, set to return the finger prosthesis into the starting position when the force transmission unit is subjected to the force of a pressure, that is to say, when the finger prosthesis swivels in the direction of the inner surface of the hand chassis. The returning force must therefore be large enough to overcome the retaining and frictional forces within the hand prosthesis.

The force transmission unit described above allows easy and inexpensive coupling of the drive and the finger prosthesis, as well as effective transmission of tensile forces. In addition, the force transmission unit provides a mounting that yields to unwanted loading and easy return.

The drives may be formed as electric motors, the first drive being formed as a relatively large, slow-running pancake motor, which is used for the displacement of the finger prosthesis relative to the hand chassis. The second drive motor, located in the respective finger prostheses, are intended for bending of the fingers or for a movement directed toward the inner surface of the hand.

In one embodiment, the second drive is located in the region of the Phalanx proximalis of a natural finger. A thumb prosthesis is a preferred application, since the proximal phalanx of the thumb is thicker than the other proximal phalanxes and so offers more space for accommodating the drive.

Since the structural space for the second drive is limited, fast-running, small motors are may be used. To be able to provide adequate adjusting force, the second drive has a gear mechanism, in particular, an inclined-screw gear mechanism, which is coupled to an output element. A speed reduction already takes place between the fast-running drive and the output element, so that the output element rotates with a much lower speed than the drive. It is therefore possible to provide not only a diversion of the direction of rotation, but also a higher drive torque.

The output element itself may be formed as a worm, which engages in and meshed with a gearwheel segment so that the output element with the gearwheel segment forms a worm gear mechanism. To avoid unwanted displacement of the second drive, together with the worm gear mechanism about the second swiveling axis, this worm gear mechanism is formed in a self-locking manner.

A composite movement of the first and second swiveling axes, aligned with preference at an angle to each other, is provided by having the second drive swivel-mounted on the gearwheel, and the gearwheel swivel-mounted on the chassis about the first swiveling axis. Consequently, the finger prosthesis can be swiveled about two axes. The complete drive, together with the screw gear mechanism and the gearwheel segment, swivel about a first swiveling axis, while the second drive swiveling about one axis on the gearwheel segment provides the second swivel movement. The angular position of the axes in relation to each other can be changed by swiveling the second drive, in order to provide a lateral grip, a neutral position or a gripping function that looks natural, or fingertip gripping of the hand prosthesis.

BRIEF DESCRIPTION OF THE DRAWINGS

An exemplary embodiment of the invention is explained in more detail below on the basis of the accompanying figures. The same designations denote the same elements in the different figures, in which.

DETAILED DESCRIPTION

Figure 1:
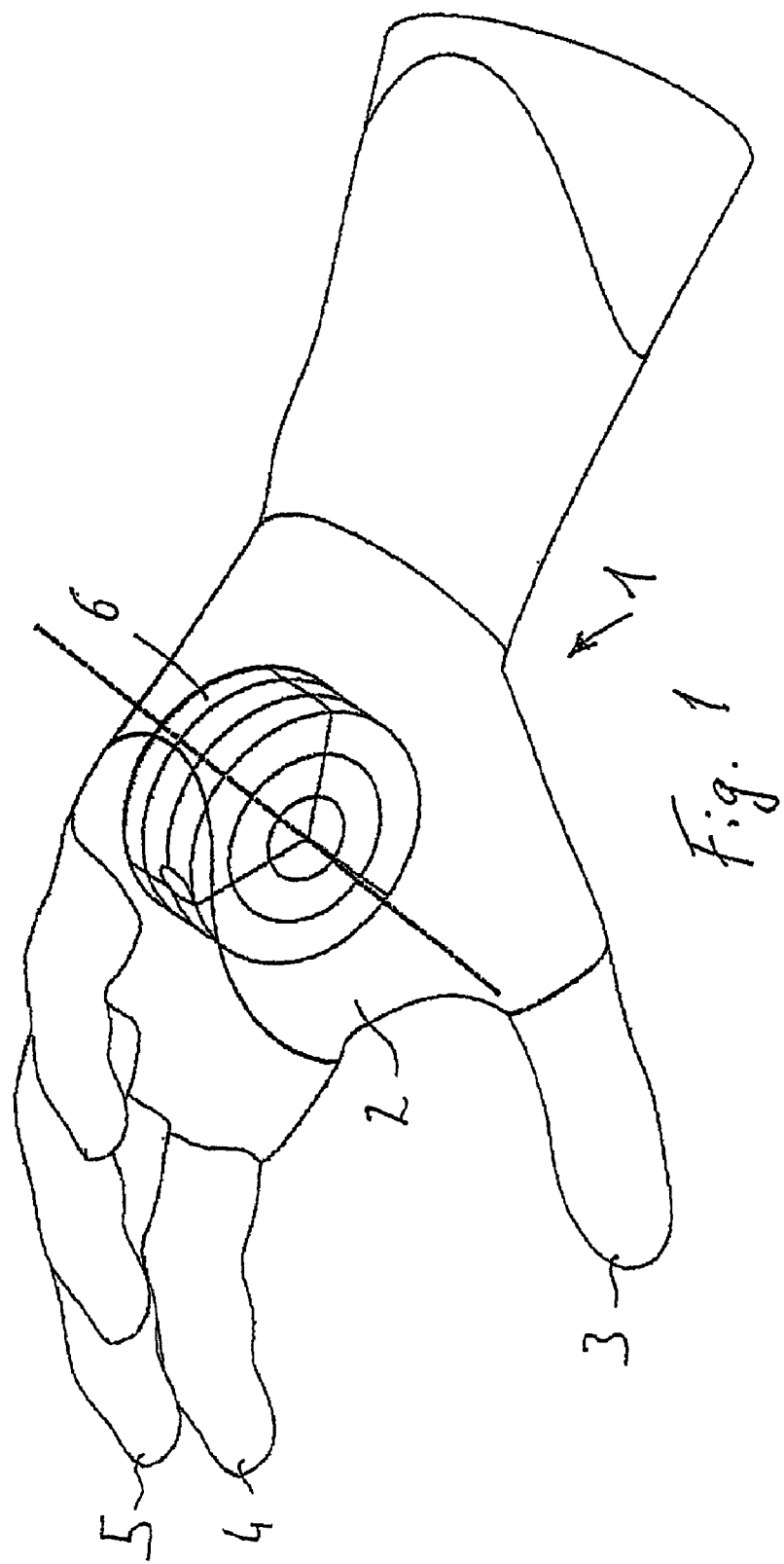
FIG. 1 shows a schematic representation of a hand prosthesis.

FIG. 1 shows a hand prosthesis 1, comprising a hand chassis 2 and at least three finger prostheses 3, 4, 5 articulated to the hand chassis 2. The finger prostheses 3, 4, 5 correspond to the thumb, index finger and middle finger, respectively, of a natural hand. Movable mounting of these three finger prostheses 3, 4, 5, which can be actuated by means of a drive 6, allows a plurality of gripping tasks of a hand to be performed. The two other fingers, the ring finger and the small finger, can be passively moved along with the other fingers and consist of an elastomer material, to achieve an appearance that looks as natural as possible. The drive 6 is mounted within the hand chassis 2 in the form of an electric drive, for example a pancake motor, with an associated gear mechanism (as shown in other figures). A power source for the drive 6 (not shown or represented), may likewise be located within the hand chassis 2. The drive 6 is activated by means of a control device (also not shown), which may likewise be located in the hand chassis 2. The corresponding signals may be generated by means of a remote control or take the form of myoelectrical signals.

Figure 2:
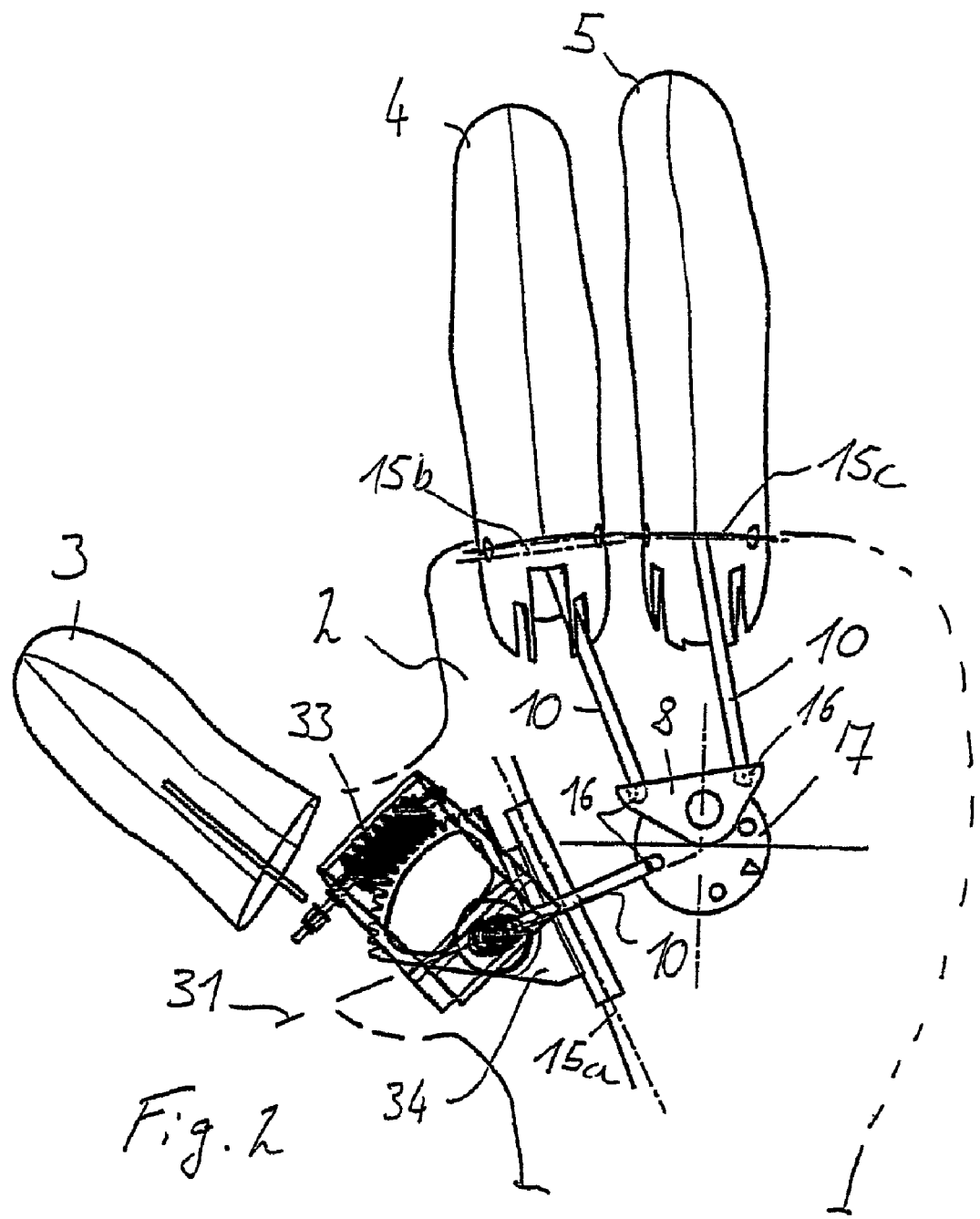
FIG. 2 shows a schematic partial representation of the functional setup of a hand prosthesis.

FIG. 2 is a schematic representation of the functional mode of the hand prosthesis 1. The three finger prostheses 3, 4, 5 are mounted on the hand chassis 2 such that they can swivel about articulating axes 15a-c. The finger prostheses 3, 4, 5 are connected via force transmission units 10, (the construction of which is described in detail further below), to a rotary disk 7, which is driven by the electric motor drive 6. The force transmission units 10 are mounted on the rotary disk 7 on spindles 16, either directly or by way of a rocker 8. The index finger 4 and the middle finger 5 are coupled to each other by way of the rocker 8, which is rotatably mounted on the rotary disk 7. The rotary disk 7 itself is mounted either directly on an output shaft of the drive 6 or on an output shaft of a gear-mechanism mounted to the drive 6.

If the drive 6 is activated, the rotary disk 7 is moved a corresponding rotational angle. As a result, the spindles 16 are displaced in relation to the swiveling-axes 15a-c of the finger prostheses 3, 4, 5, which leads to a swiveling of the finger prostheses 3, 4, 5. This is due to the tensionally rigid formation of the force transmission units 10 and an articulation of the force transmission units 10 on the finger prostheses 3, 4, 5 that is at a distance from the axes of rotation 15a-c. If the drive 6 is reversed and the rotary disk 7 moves into a position in which the spindles 16 are at a minimal distance from the swiveling axes 15a-c of the finger prostheses 3, 4, 5, the opened starting position of the rotary disk 7 and drive 6 is reached. The finger prostheses 3, 4, 5 then move into their opened starting position, as a result of the resiliently elastic properties of the force transmission units 10. It is provided here that the force transmission units 10 can transmit much higher tensile forces than compressive forces. This corresponds to the physiological conditions of a natural hand, which can apply much greater forces when closing the hand than when opening it. For reasons of overall clarity, the ring finger and the small finger are not represented; they can be passively articulated to the middle finger 5 and thereby moved along with it.

In FIG. 2, it can also be seen that, apart from the first swiveling axis 15a, the thumb prosthesis 3 has a second swiveling axis 31 (coming out of the page at an angle), about which at least the distal end of the thumb prosthesis 3 is swivel-mounted. A second drive 30 and an inclined-screw gear mechanism 32 (both shown in FIG. 4) are used to move an output worm 33. The worm 33 meshes with a gearwheel segment 34 to bring about a displacement of the finger prosthesis 3, including the drive 30 and the gear mechanism 32, about the swiveling axis 31. If both drives 6, 30 are activated at the same time, a combined movement of the thumb prosthesis 3 in the palmar and ulnar directions is performed in accordance with the displacement speeds, which corresponds to the natural mobility of a thumb.

Figure 3A:
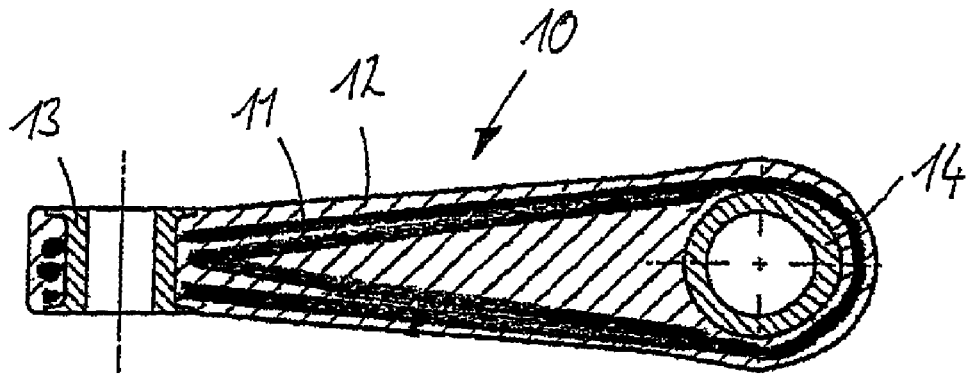
FIGS. 3a-3c show a force transmission unit in different views.

FIG. 3a shows a force transmission unit 10 in a sectional representation. This unit 10 comprises a cable or fiber component 11, which in the present case is formed as a loop. The cable component 11 may comprise a number of standard wires or individual loops, take the form of a steel cable or plastic cable, or include some other high-strength fiber material. The cable component 11 is embedded in an elastomer element or component 12, whereby the force transmission unit 10 is given a dimensionally stable, but flexurally elastic, form. The elastomer component 12 may include a silicone, a rubber or some other elastic material. In spite of the dimensional stability, a deformation, in particular bending, caused by compressive forces acting on the force transmission unit 10 is possible. The deformation is a result of the flexibility of the cable or fiber component 11 and the elastic characteristics under pressure or bending of the elastomer component 12. This allows the finger prostheses 3, 4, 5 that are coupled to the drive 6 or the rotary disk 7 via the force transmission unit 10 to be displaced in the direction of the inner surface of the hand chassis 2 by the compressive forces. A return displacement takes place as a result of the resiliently elastic characteristics of the force transmission units 10, when the corresponding counteracting compressive force is no longer applied.

Located within the loop of the cable or fiber component 11 are two bearing-bushings 13, 14, which are likewise embedded in the elastomer component 12. The bearing bushings 13, 14 are mounted on corresponding spindles on the finger prostheses 3, 4, 5 and on spindles 16 on the rotary disk 7 or the rocker 8. The bearing-bushings 13, 14 are made, for example, of bronze, in order to form a sliding mounting with the corresponding spindles 16. For reasons of overall clarity, the coupling spindles on the finger prostheses 3, 4, 5 are not represented. These coupling spindles lie at a distance from the axes of rotation 15a-c. Thus, a torque is produced about the axes of rotation 15a-c by applying tensile forces via the force transmission units 10, which leads to a corresponding displacement of the finger prostheses 3, 4, 5.

Figure 3B:
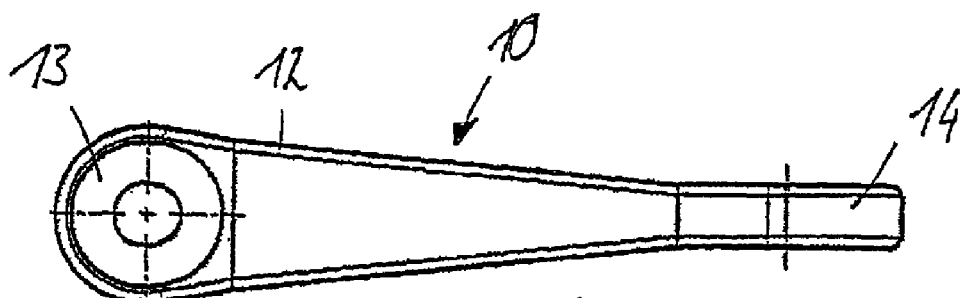
Figure 3C:
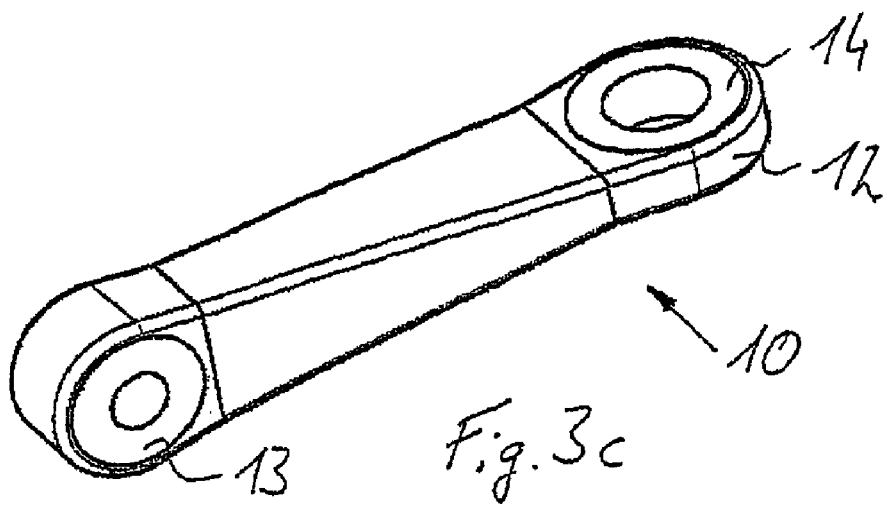

In FIGS. 3b and 3c, it can be seen that the axes of rotation of the bearing bushings 13, 14 are perpendicular in relation to each other. The reason for this is due to the actual arrangement of the rotary disk 7 and the spindles 16 arranged on it or assigned to it. The axes of rotation of the bearing bushings 13, 14 may also be aligned parallel or at some other angle in relation to each other.

It can likewise be seen in FIGS. 3a to 3c, that the cable or fiber component 11 is completely embedded in the elastomer 12. On the one hand, the cable or fiber component 11 is thereby protected from external influences and, on the other hand, the dimensional stability of the force transmission unit 10 is increased.

In another embodiment, the force transmission unit 10 may also be produced from some other element or material that yields under pressure. One example is a resiliently elastic and tensionally rigid element, such as a resilient buckling or deflecting rod or a correspondingly designed wire loop.

The compressively elastic mounting described above keeps impact forcest from being directly transmitted via the finger prostheses 3, 4, 5 to the drive 6 or the rotary disk 7. Rather, unintentional knocking movements are absorbed and damped. Apart from enhancing a natural looking appearance of the hand prosthesis 1, this also increases the service life of the mountings and drive components, for example in the event of a fall.

In another embodiment, the spring-damper force transmission unit 10 may also be equipped with a corresponding control, for example by means of a pneumatic or hydraulic cylinder with corresponding valve control. The unit 10 can thus effectively transmit tensile forces but provides the ability to yield elastically under compressive forces. A pneumatic configuration has the effect of bringing about a return displacement of the inwardly bent finger prostheses.

Given an adequately flexurally elastic configuration of the cable component 11, the elastomer component 12 may be omitted. Given adequate tensile strength of the elastomer component 12, it may be formed as the only force transmission unit 10.

Figure 4:
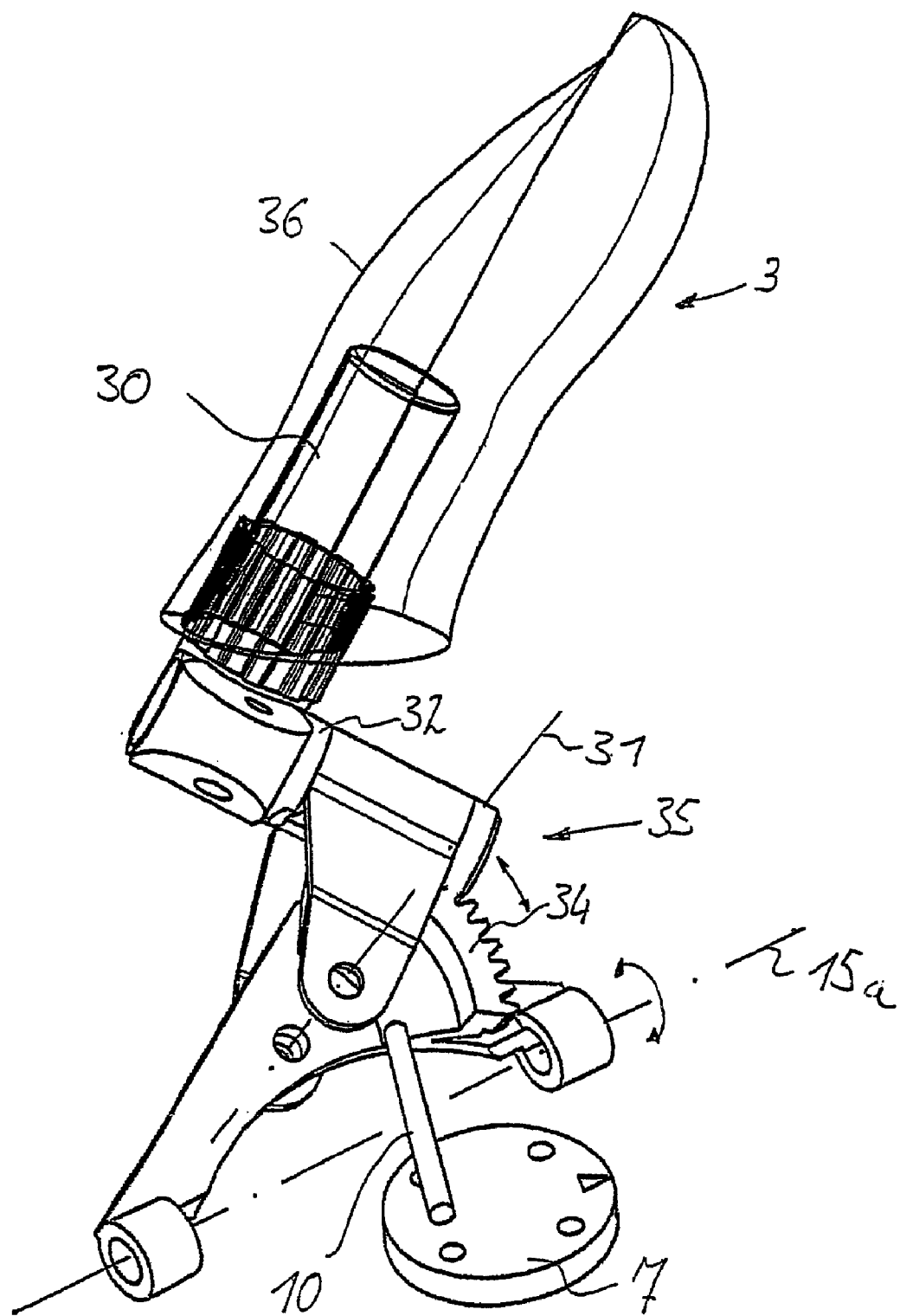
FIG. 4 shows a functional setup of a finger prosthesis.

FIG. 4 is a detailed representation of the functional setup of the thumb prosthesis 3, comprising a molding 36, which replicates the contour of a natural thumb. Inside the molding 36, which is formed as a hollow body, there is a free space, in which the second drive 30 is located and fastened. The molding 36 is consequently coupled, for example adhesively attached or firmly clamped, to the drive 30. The drive 30 is coupled to the gearwheel segment 34 by means of an angular gear mechanism in the form of an inclined-screw gear mechanism 32 and the worm 33 (shown and described in FIG. 2).

On activation of the drive 30, the worm 33 is turned in one direction or the other. On account of the swivel-mounting about the axis of rotation 31 on the gearwheel segment 34, a movement about the swiveling axis 31 is possible in the direction of the double-headed arrow. A radial or ulnar movement may thereby be performed. The gearwheel segment 34 itself is swivel-mounted about the first swiveling axis 15a and can be swiveled in a palmar or dorsal direction by a turning of the rotary disk 7 and the corresponding displacement of the force transmission element 10. This swiveling movement is likewise indicated by the double-headed arrow around the swiveling axis 15a.

The second drive 30 is likewise an electric drive, for example an electric motor or piezoelectric motor, and is preferably located along the longitudinal axis between what would be the carpometacarpal joint and the interphalangeal joint. On account of the small type of construction and the possibly necessary high drive torque, the drive 30 is formed as a fast-running motor. The speed-transforming gear mechanism 32 is formed as an inclined-screw gear mechanism producing an approximately right-angled deflection of the drive axis in relation to the longitudinal axis of the second drive 30. On account of this angling away of the output spindle, it is possible for the worm 33, which meshes with the gearwheel segment 34, to bring about a corresponding movement of the thumb. As an alternative to a substantially right-angled deflection, any desired angular position can also be realized by a corresponding configuration of the gear mechanism 32, for example +45° in relation to a right-angled alignment.

The first drive 6, arranged in the hand chassis 2, is a slow-running pancake motor with a high torque, which is coupled to a highly speed-reducing gear mechanism 32, to allow a correspondingly slow gripping movement to be performed. The control signals may either be generated by a remote control or be myoelectrical signals and have a control device. By means of this first drive 6 and the rotary disk 7, it is possible to displace the gearwheel segment 34 together with the worm 33, as well as the gear mechanism 32 and the drive 30 covered by the molding 36.

The invention claimed is:

1. A hand prosthesis comprising:
   a chassis;
   a finger prosthesis articulated to the chassis;
   a first drive located in the chassis and coupled to the finger prosthesis, the first drive moving the finger prosthesis about a first swiveling axis relative to the chassis;
   a force transmission unit located in the chassis coupling the finger prosthesis to the first drive; and
   a second drive located within the finger prosthesis such that the second drive moves with the finger prosthesis when the first drive moves the finger prosthesis about the first swiveling axis, the second drive coupled via a gear mechanism to an output device, the output device including a worm element positioned to mesh with a gearwheel segment to form a worm gear mechanism, the second drive moving a portion of the finger prosthesis in which the second drive is located about a second swiveling axis that does not intersect with the first swiveling axis.

2. The hand prosthesis as claimed in claim 1, wherein the drives are decoupled from each other.

3. The hand prosthesis as claimed in claim 1, wherein the force transmission unit is rigid under tension and yielding under pressure or elastic under bending.

4. The hand prosthesis as claimed in claim 1, wherein the force transmission unit comprises a cable, a fiber component or a stranded wire.

5. The hand prosthesis as claimed in claim 4, wherein the cable, the fiber component or the stranded wire comprises a closed, open or twisted loop.

6. The hand prosthesis as claimed in claim 4, wherein the force transmission unit further comprises an elastomer component.

7. The hand prosthesis as claimed in claim 6, wherein the elastomer component at least partially encloses the cable, the fiber component or the stranded wire.

8. The hand prosthesis as claimed in claim 1, wherein the force transmission unit comprises an elastomer component.

9. The hand prosthesis as claimed in claim 1, wherein the force transmission unit comprises bearing bushings for receiving spindles that are provided by the hand chassis and the finger prosthesis, with the hand chassis spindles directly or indirectly mounted to the first drive and the finger prosthesis spindles mounted within the finger prosthesis.

10. The hand prosthesis as claimed in claim 1, wherein the force transmission unit is formed in a resiliently elastic manner.

11. The hand prosthesis as claimed in claim 10, wherein a spring rate of the force transmission unit is set to return the finger prosthesis into a starting position when the force transmission unit is subjected to a force due to pressure applied to the finger prosthesis.

12. The hand prosthesis as claimed in claim 1, wherein the drives comprise electric motors.

13. The hand prosthesis as claimed in claim 1, wherein the second drive is located in the finger prosthesis in a region corresponding to the Phalanx proximalis of a natural finger.

14. The hand prosthesis as claimed in claim 1, wherein the second drive is swivel-mounted on the gearwheel segment.

15. The hand prosthesis as claimed in claim 14, wherein the gearwheel segment is swivel-mounted on the chassis.

16. The hand prosthesis as claimed in claim 1, wherein the worm gear mechanism is self-locking.

17. The hand prosthesis as claimed in claim 1, wherein the gearwheel segment is swivel-mounted on the chassis.

18. The hand prosthesis as claimed in claim 1, wherein the second drive moves the finger prosthesis between a number of fixed positions.

19. A hand prosthesis comprising:
   a chassis;
   a finger prosthesis articulated to the chassis;
   a first drive located in the chassis and coupled to the finger prosthesis, the first drive moving the finger prosthesis about a first swiveling axis relative to the chassis;
   a force transmission unit located in the chassis coupling the finger prosthesis to the first drive; and
   a second drive located within the finger prosthesis such that the second drive moves with the finger prosthesis when the first drive moves the finger prosthesis about the first swiveling axis, the second drive coupled via a gear mechanism to an output device, the output device including a worm element positioned to mesh with a gearwheel segment to form a worm gear mechanism, the second drive moving a portion of the finger prosthesis in which the second drive is located about a second swiveling axis that is at an angle relative to the first swiveling axis.

* * * * *